US010376362B2

(12) United States Patent
Costello et al.

(10) Patent No.: US 10,376,362 B2
(45) Date of Patent: Aug. 13, 2019

(54) VALVE INTRODUCERS WITH ADJUSTABLE DEPLOYMENT MECHANISM AND IMPLANTATION DEPTH GAUGE

(75) Inventors: Declan Costello, Ballinrobe (IE); Ronan Rogers, Galway City (IE); Edmond Sheahan, Galway (IE); Damian Carr, Oranmore (IE)

(73) Assignee: Medtronic Vascular Galway, Galway (IE)

( * ) Notice: Subject to any disclaimer, the term of this patent is extended or adjusted under 35 U.S.C. 154(b) by 1021 days.

(21) Appl. No.: 13/440,967

(22) Filed: Apr. 5, 2012

(65) Prior Publication Data
US 2013/0268065 A1    Oct. 10, 2013

(51) Int. Cl.
*A61F 2/24* (2006.01)
*A61F 2/95* (2013.01)

(52) U.S. Cl.
CPC .......... *A61F 2/2427* (2013.01); *A61F 2/2433* (2013.01); *A61F 2002/9517* (2013.01); *A61F 2250/0007* (2013.01); *A61F 2250/0065* (2013.01); *A61F 2250/0097* (2013.01)

(58) Field of Classification Search
CPC ............ A61F 2/2418; A61F 2002/9522; A61F 2/2427; A61F 2/966
USPC ........................................................ 623/2.11
See application file for complete search history.

(56) References Cited

U.S. PATENT DOCUMENTS

| 7,914,569 B2 | 3/2011 | Nguyen et al. |
| 8,016,877 B2 | 9/2011 | Seguin et al. |
| 2004/0210304 A1* | 10/2004 | Seguin et al. ............... 623/2.11 |
| 2005/0149159 A1* | 7/2005 | Andreas ................... A61F 2/95 623/1.11 |
| 2010/0286768 A1* | 11/2010 | Alkhatib ............... A61F 2/2418 623/2.11 |
| 2010/0292782 A1 | 11/2010 | Giannetti et al. |
| 2011/0282425 A1 | 11/2011 | Dwork |
| 2012/0053574 A1 | 3/2012 | Murray et al. |
| 2012/0123528 A1* | 5/2012 | Knippel et al. .............. 623/2.11 |
| 2014/0107771 A1* | 4/2014 | Berreklouw ................. 623/2.11 |

FOREIGN PATENT DOCUMENTS

| DE | 202010005388 | 7/2010 |
| EP | 0418677 | 3/1991 |
| WO | WO2012/023980 | 2/2012 |

\* cited by examiner

*Primary Examiner* — Phong Son H Dang
(74) *Attorney, Agent, or Firm* — Medler Ferro Woodhouse & Mills PLLC

(57) ABSTRACT

Valve introducer systems and methods for implanting heart valve prostheses are disclosed, where a valve introducer includes an adjustable deployment mechanism comprising a deployment element and an implantation depth controlling element having a distal end and an adjustable length. The valve introducer also includes a tubular member having a distal end, configured to deliver a heart valve prosthesis, and a length extending from a fixed reference point. The implantation depth controlling element can comprise an inner and an outer cylinder, such as where the outer cylinder has interior threads, and the inner cylinder has exterior threads. The adjustable deployment element can include a depth gauge, wherein the depth gauge indicates the length the tubular member extends beyond a fixed reference point. In certain embodiments, the adjustable deployment element can also be configured to be secured to a cannula.

20 Claims, 3 Drawing Sheets

VALVE INTRODUCERS WITH ADJUSTABLE DEPLOYMENT MECHANISM AND IMPLANTATION DEPTH GAUGE

BACKGROUND OF THE INVENTION

Field of the Invention

The present invention relates to systems and methods for delivering a prosthesis to a desired location in the body of a patient and methods for delivering and implanting a prosthesis. More particularly, the present invention relates to valve introducer systems for deploying heart valve prostheses within a body lumen and to methods of delivering such prostheses to a desired location in the body. The valve introducer system includes an adjustable deployment mechanism with an implantation depth controlling element and depth gauge to facilitate accurate deployment of the heart valve prosthesis.

Background

Currently, the replacement of a deficient cardiac valve is often performed by opening the thorax, placing the patient under extracorporeal circulation, temporarily stopping the heart, surgically opening the heart, excising the deficient valve, and then implanting a prosthetic valve in its place. This procedure generally requires prolonged patient hospitalization, as well as extensive and often painful recovery.

Recently, minimally invasive approaches have been developed to facilitate catheter-based implantation of valve prostheses in the beating heart, intending to obviate the need for the use of classical sternotomy and cardiopulmonary bypass. For example, U.S. Pat. No. 8,016,877 to Seguin et al. illustrates a technique and a device for replacing a deficient heart valve by percutaneous route. An expandable prosthetic valve is compressed about a catheter, inserted inside a lumen within the body, such as the femoral artery, and delivered to a desired location in the heart. Additionally, U.S. Pat. No. 7,914,569 to Nguyen et al. discloses advancing the catheter containing the prosthesis in a retrograde manner through the femoral artery and into the descending aorta, over the aortic arch, through the ascending aorta and inside the defective aortic valve. This procedure can be assisted by fluoroscopic guidance. Once the position of the catheter containing the prosthesis is confirmed, a sheath containing the prosthesis can be moved proximally, allowing the valve prosthesis to self-expand.

However, in certain instances it may still be necessary to use the classic sternotomy technique. It would be desirable though to avoid cardiopulmonary bypass during the procedure while still obtaining accurate positioning of the prosthetic valve.

With regard to implantation of the heart valve prosthesis and the structure of the prosthesis itself, U.S. Pat. No. 7,914,569 to Nguyen et al. describes an exemplary prosthesis for percutaneous transluminal delivery. The heart valve prosthesis can have a self-expanding multi-level frame that supports a valve body with a skirt and plurality of leaflets. The frame can be contracted during percutaneous transluminal delivery and expanded to an hourglass shape upon deployment within the native heart valve.

Other techniques for delivering prosthetic heart valves via a catheter include a transapical approach for aortic valve replacement, typically involving the use of an introducer port, i.e., a large-bore overtube, of a trocar. A crimped, framed valve prosthesis reversibly coupled to a delivery catheter is transcatheterally advanced toward the native valve, where it is either deployed using a balloon catheter, or, alternatively, using a self-expandable system.

The present invention provides valve introducer systems for implanting a heart valve prosthesis through a trans-aortic pathway. The valve introducer includes an adjustable deployment mechanism with a implantation depth controlling element to precisely set the depth a tubular delivery member extends into the body of a patient. By directly accessing the aorta, it is an object of this invention to accurately implant a prosthetic valve without the need for cardiopulmonary bypass, although the disclosed valve introducer systems can also be used with cardiopulmonary bypass.

BRIEF SUMMARY OF THE INVENTION

The present invention provides valve introducer systems for accurate implantation of a heart valve prosthesis during a sternotomy, or a minimally invasive procedure with direct access to the aorta, without the need for cardiopulmonary bypass. The valve introducers include an adjustable deployment mechanism with implantation depth controlling element to precisely set the depth a tubular delivery member extends into the body of a patient. In one embodiment, the implantation depth controlling element can be an outer cylinder with interior threads and an interior cylinder with exterior threads. By twisting the cylinders in opposite directions, the length of the adjustable deployment mechanism, and thus the depth the tubular delivery member extends into the body of a patient, can be increased or decreased. A depth gauge on the adjustable deployment mechanism can display the depth the tubular delivery member extends beyond a fixed reference point into a patient's body. The adjustable deployment mechanism can be configured to couple with a cannula, which itself can be fastened to the aorta during the implantation procedure to eliminate unwanted movement of the valve introducer system.

BRIEF DESCRIPTION OF THE FIGURES

The accompanying figures, which are incorporated herein, form part of the specification and illustrate embodiments of valve introducer systems and methods of delivering prostheses to a desired location in the body of a patient. Together with the description, the figures further serve to explain the principles of and allow for the making and using of the valve introducer systems and methods described herein. In the drawings, like reference numbers indicate identical or functionally similar elements.

DETAILED DESCRIPTION OF THE INVENTION

The following detailed description of valve introducer systems and methods of delivering prostheses to a desired location in the body of a patient refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

Figure 1:
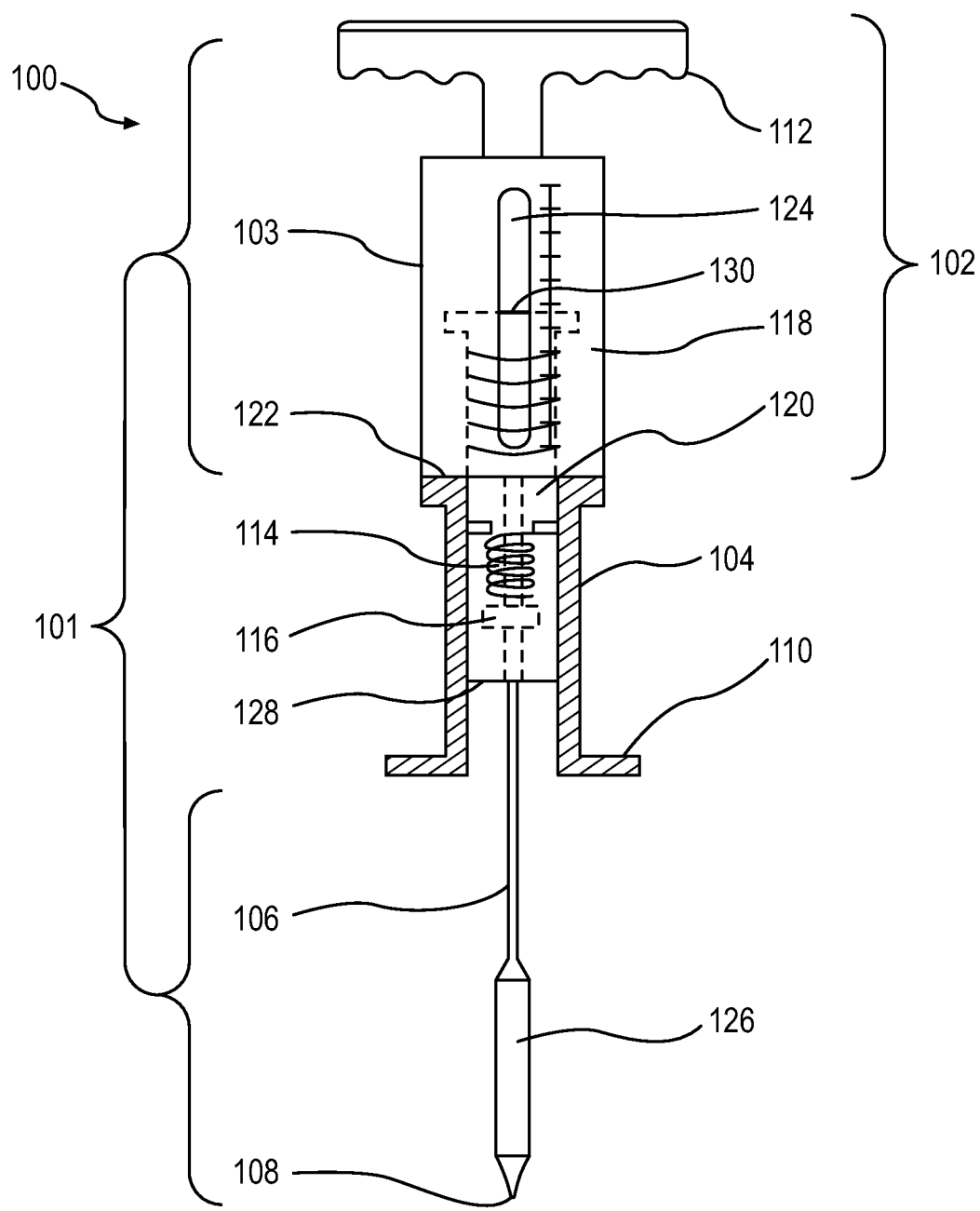
FIG. 1 illustrates a valve introducer system in accordance with one embodiment presented herein, including a partial interior view.

FIG. 1 illustrates a valve introducer system 100 in accordance with one embodiment presented herein with a partial interior view. In one embodiment, the valve introducer system 100 also includes a cannula 104. The valve introducer 101 generally includes an adjustable deployment mechanism 102, having a deployment element 112 and an implantation depth controlling element 103 with a depth gauge 124. The valve introducer 101 also includes a tubular member 106 configured to deliver a heart valve prosthesis (not shown). In certain embodiments, the adjustable deployment mechanism 102 includes a cannula engagement surface 122 so that the adjustable deployment mechanism 102 can be coupled with a cannula 104.

The implantation depth controlling element 103, as the name implies, is a mechanism or device that controls the depth that the tubular member 106 extends beyond a fixed reference point, such as the exterior surface of the aorta or the distal end 128 of the implantation depth controlling element 103, into a patient's body. The implantation depth controlling element 103 is adjustable, meaning that its length can be made shorter or longer by physical manipulation. Also, in certain embodiments, the implantation depth controlling element 103 can be locked once its length is set. Generally, once the implantation depth controlling element 103 is set at the predetermined delivery depth, it is not intended to be adjusted during the delivery procedure. However, in certain embodiments, the implantation depth controlling element 103 can be adjusted during the delivery procedure if the surgeon determines that the distal end 108 of the tubular member 106 is not in the proper place within the body of a patient to deploy the heart valve prosthesis.

The implantation depth controlling element 103 can be made from a variety of materials, including plastics, metals or any other suitable material. In one embodiment, the implantation depth controlling element 103 of the adjustable deployment mechanism 102 includes an outer cylinder 118 and an inner cylinder 120. Generally, the diameter of the inner cylinder 120 should be such that it can fit inside a cannula 104, as depicted in FIG. 1. The outer cylinder 118 can include interior threads and the inner cylinder 120 can include exterior threads. In certain embodiments, both cylinders can be twisted relative to each other to make the implantation depth controlling element 103 longer or shorter. In other embodiments, one of the cylinders, generally the inner cylinder 120, is fixed, and only one cylinder, generally the outer cylinder 118, twists relative to the other cylinder.

Other embodiments of the implantation depth controlling element 103 are contemplated. One embodiment includes a telescopic implantation depth controlling element 103, where the inner cylinder 120 can slide in both the proximal and distal directions within the outer cylinder 118. The outer cylinder 118 can have a collar configured to tighten about the inner cylinder 120, thereby setting the length of the implantation depth controlling element 103 and, consequently, the depth the tubular member 106 can extend into the body of a patient. Another embodiment includes a physical stopping element that can be positioned along the implantation depth controlling element 103. For example, the physical stopping element could be a pin inserted at a point along the depth gauge 124 that prevents the inner cylinder 120 from moving past it, thus dictating the depth the tubular member 106 can extend into the body of a patient.

In order for a heart valve prosthesis to function optimally, it should be implanted accurately within the native valve. Therefore, it is important to know the depth the tubular member 106 will extend into the body because that is where the prosthesis will be deployed. A depth gauge 124 therefore facilitates accurate deployment by displaying the depth the tubular member 106 will extend into the body relative to an insertion point on the patient's anatomy. For this reason, certain embodiments of the valve introducer system 100 can include a depth gauge 124.

Figure 3:
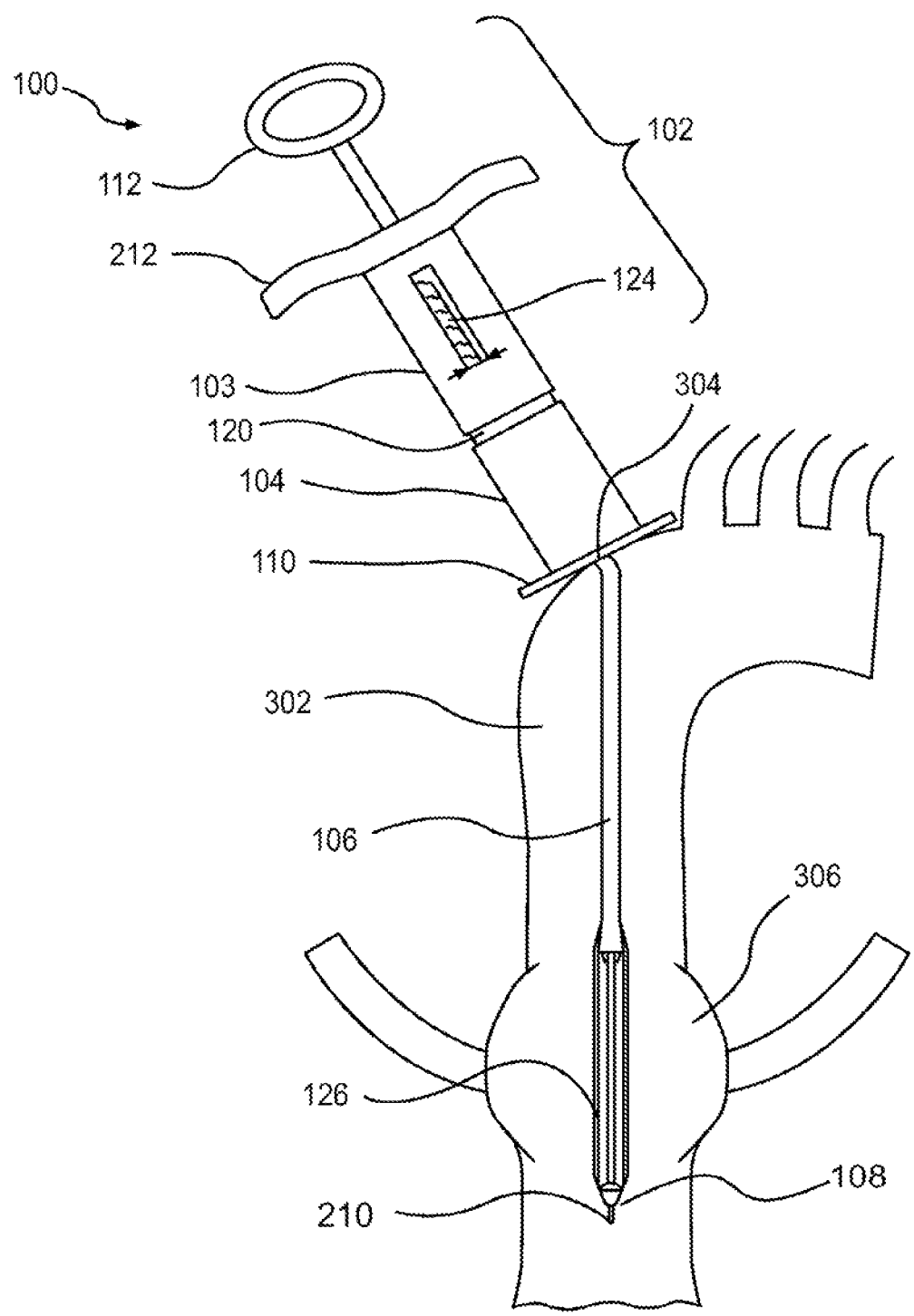
FIG. 3 illustrates a valve introducer system with deployment of a tubular member carrying a heart valve prosthesis into an aorta and aortic sinus.

The depth gauge 124 can display the depth the distal end 108 of the tubular member 106 extends beyond a fixed reference point into a patient's body. The reference point can be, but is not limited to, the exterior surface of the aorta or the distal end 128 of the implantation depth controlling element 103. In certain embodiments, the depth gauge 124 can include a "window" made of transparent material such as plastic or glass, and can include markings indicating units of length, as shown in FIG. 3. By adjusting the implantation depth controlling element 103, the proximal end 130 of the inner cylinder 120 can be aligned with a unit of length marking, indicating how far the distal end 108 of the tubular member 106 will extend beyond the fixed reference point. Alternatively, the inner cylinder 120 can have unit of length markings, which can be aligned with a marker, such as an arrow, on the window of the depth gauge 124 in order to indicate the depth the tubular member 106 will extend into the body of the patient. In another embodiment, the unit of length markings can be indicated on the outer cylinder 118, such as by painting or etching, as shown in FIG. 1. In still another embodiment, the depth gauge 124 can be configured to provide a digital readout of the depth the tubular member 106 will extend into the body of the patient.

The deployment element 112 can be used to deploy the heart valve prosthesis within the body. Any deployment element known in the field may be used, such as those described in U.S. patent application Ser. Nos. 13/106,110 and 13/219,895. Generally, these mechanisms can be operated with one hand, whereby pushing or twisting the deployment element retracts a sheath covering the heart valve prosthesis.

Figure 2:
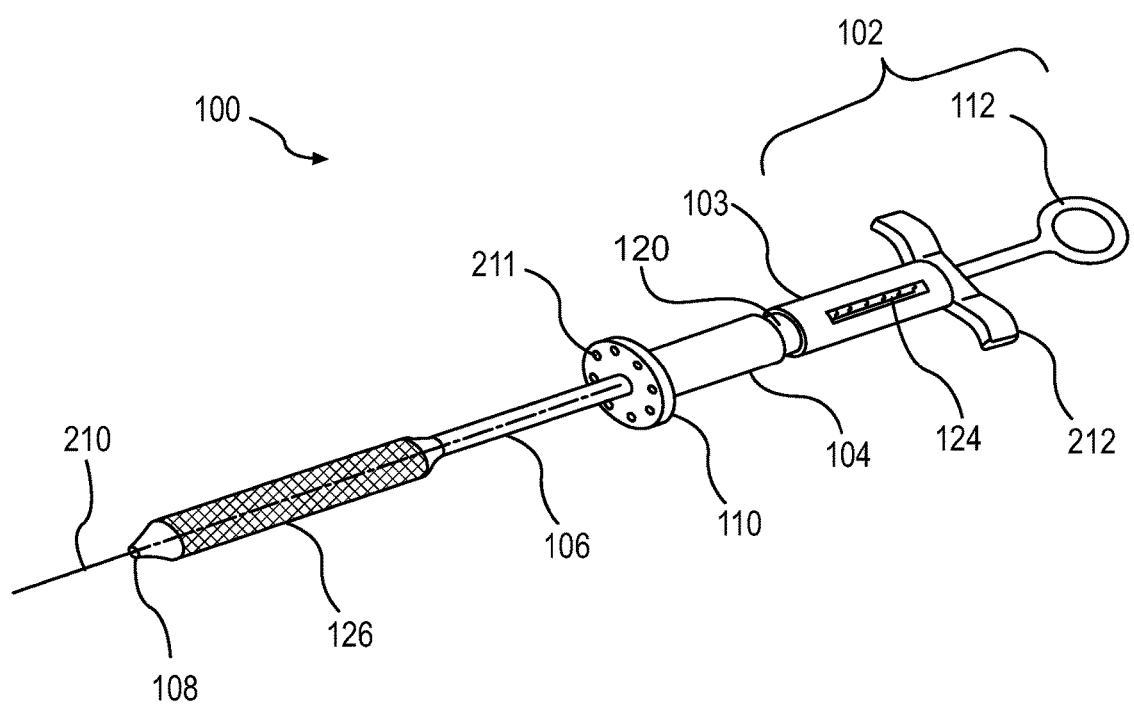
FIG. 2 illustrates an exterior view of a valve introducer system in accordance with one embodiment presented herein.

Further examples of the deployment element 112 are depicted in FIG. 1, where the deployment element 112 is shaped like a button, and FIG. 2, where the deployment element 112 is shaped like a syringe. In either of these embodiments, the deployment element 112 can be pushed in the distal direction, which retracts the capsule 126 in the proximal direction, uncovering a heart valve prosthesis contained within the capsule 126. The deployment element 112 can also be configured such that it can be pulled in the proximal direction to retract the capsule 126 and thereby uncover the heart valve prosthesis. Alternatively, deployment element 112 can be a thumbwheel such as those known in the art, whereby rotating the thumbwheel causes the capsule 126 to retract in the proximal direction, thereby uncovering the heart valve prosthesis contained therein.

A further embodiment of the deployment element 112 includes a spring 114 to provide tactile feedback to the deployment element 112 when deploying the heart valve prosthesis, particularly with the syringe type deployment element. As the deployment element 112 is pushed in the distal direction, a spring contact surface 116 on the tubular member 106 contacts the spring 114, which provides tactile resistance in order to smoothly uncover the heart valve prosthesis within the capsule 126.

The tubular member 106 can be used as the delivery element for the heart valve prosthesis. The prosthesis can be radially collapsed and loaded inside or at the end of the tubular member 106. A capsule 126 can cover the prosthesis until it is ready to be deployed. In certain embodiments, the capsule 126 can be a sheath. The tubular member 106 can be a catheter of the type known in the art used for delivering prosthetic valves through the vascular system, and can be made of any suitable material, such as plastic. The material should be rigid enough to support delivery of the heart valve prosthesis in a retrograde direction, yet flexible enough so as to not damage the interior vascular wall during delivery. Generally, the length of the tubular member 106 is fixed and the depth the distal end 108 of the tubular member 106 extends into the body beyond a reference point can be controlled by adjusting the implantation depth controlling element 103.

Although the valve introducer 101 can be its own separate device, in certain embodiments, it can be coupled with a cannula 104. This can facilitate deployment of the heart valve prosthesis because the cannula 104 can be secured to the aorta 302, providing a steady access point for the valve introducer 101 to enter the body.

As shown in FIG. 1, in one embodiment, the adjustable deployment mechanism 102 has a cannula engagement surface 122, such that the adjustable deployment mechanism 102 can be coupled with a cannula 104. The cannula engagement surface 122 can be a flat horizontal surface that allows the adjustable deployment mechanism 102 to rest on top of the cannula 104. In certain embodiments, however, the cannula engagement surface 122 includes a locking mechanism to secure the adjustable deployment mechanism 102 to the cannula 104. The locking mechanism can include threading such that by twisting the adjustable deployment mechanism 102 it engages threading on the cannula 104 to secure the two together. Alternatively, the locking mechanism can include at least one protrusion or groove such that the cannula engagement surface 122 clicks with or snaps together with the cannula 104.

FIG. 2 depicts another embodiment of the valve introducer system 100. The adjustable deployment mechanism 102 in FIG. 2 includes a syringe style deployment element 112. The deployment element 112 can have an eyelet, as pictured, or can take various other forms. In this embodiment, the adjustable deployment mechanism includes handles 212 which can be gripped to steady the valve introducer 101 during deployment of the heart valve prosthesis and allow for one-handed deployment of the prosthesis.

FIG. 2 also depicts one embodiment of a fastening element 110 on the cannula 104. The fastening element 110 shown is a surface including suture holes 211. In this embodiment, the surface of the fastening element 110 can be placed in contact with the outside of the aorta and sutures can be made through the suture holes 211 to secure the cannula 104 to the aorta. This helps minimize movement of the valve introducer system 100 during the delivery of the heart valve prosthesis.

Other embodiments of the fastening element 110 are contemplated. For example, the fastening element 110 can be a belt or a collar that wraps around the aorta and can be secured to keep the valve introducer system 100 steady during deployment of the heart valve prosthesis.

FIG. 2 further depicts a guide wire 210 for the tubular member 106. The guide wire 210 can help the tubular member 106 travel smoothly through the artery and can reduce contact of the tubular member 106 with the interior artery wall. The guide wire 210 can be made from any material generally used in the field for wires that aid the travel of catheters through the vascular system.

FIG. 3 depicts one embodiment of the valve introducer system 100 delivering a heart valve prosthesis. In this embodiment, the adjustable deployment mechanism 102 has a syringe style deployment element 112 and is attached to a cannula 104.

Prior to surgery, the depth the tubular member 106 should extend into the body of the patient should be determined. This can be done with the aid of medical imaging, such as a CT scan, by determining an insertion point 304 and calculating the depth to the desired implantation site. Generally, the implantation site is located within the aortic sinus 306 such that the prosthetic valve is deployed so that the distal part of the prosthesis engages the leaflets of the natural aortic valve and the proximal part of the prosthesis engages the inner wall of the ascending aorta. Alternative implantation sites can be used, and the optimal implantation site can be determined by a physician for each individual patient.

The optimal depth from the insertion point 304, or other fixed reference point, to the distal end 108 of the tubular member 106 can be calculated based on a patient's anatomical landmarks. This depth can be set on the valve introducer 101 by adjusting the implantation depth controlling element 103, and it can be displayed on the depth gauge 124.

Generally, the patient's thorax will be opened such that the aorta 302 is exposed, and an incision can be made at an insertion point 304 on the aorta 302. The aorta, as defined herein, can include the exterior surface and lumen of the descending aorta, aortic arch, ascending aorta and aortic sinus. A valve placed at the insertion point 304 can prevent blood from exiting the body. A cannula 104 can be secured to the aorta 302 at the insertion point 304 with a fastening element 110.

A radially collapsed heart valve prosthesis can be loaded into a capsule 126 at the distal end 108 of the tubular member 106, and the valve introducer 101 can be coupled with the cannula 104 secured in place at the insertion point 304 by the fastening element 110. As the valve introducer 101 is coupled with the cannula 104, the tubular member 106 can extend retrograde within the aorta 302 until the distal end 108 of the tubular member 106 reaches the desired implantation location near the distal part of the aortic sinus 306. The location of the distal end 108 of the tubular member 106 can be checked by medical imaging. In certain embodiments, the implantation depth controlling element 103 can be adjusted to move the distal end 108 of the tubular member 106 in either the distal or proximal direction if the cardiologist determines that the position of the distal end 108 of the tubular member 106 is not in the proper deployment position.

Once in the proper position, the deployment element 112 can be activated, which causes the capsule 126 to move in the proximal direction, thereby uncovering the heart valve prosthesis contained in the capsule 126. The prosthesis can be self-expanding or can be mechanically expanded, such as by balloon inflation. After the prosthesis is fully deployed, the tubular member 106 can be removed from the aorta 302 via the insertion point 304 by moving the valve introducer 101 in the proximal direction. The cannula 104 can be detached from the aorta 302, and the incision at the insertion point 304 can be closed by sutures.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

We claim:

1. A valve introducer system comprising a valve introducer, the valve introducer comprising:
   a tubular element configured to deliver a heart valve prosthesis, wherein the tubular element includes an outer shaft configured to house a heart valve prosthesis therein and an inner shaft, the tubular element having a length extending from a fixed reference point on the valve introducer to a distal end of the tubular element such that the inner shaft has a inner shaft length from the fixed reference point to a distal end of the inner shaft attached to a nosecone and the outer shaft has an outer shaft length from the fixed reference point to an outer shaft distal end; and
   an adjustable deployment mechanism comprising:
      a deployment element configured to move the outer shaft relative to the inner shaft upon actuation of the deployment element to uncover a heart valve prosthesis configured to be disposed within the outer shaft; and
      an implantation depth controlling element having a distal end and an adjustable length, wherein the implantation depth controlling element is configured such that adjusting the length of the implantation depth controlling element changes the length of the inner shaft with the nosecone attached thereto from the fixed reference point to the distal end of the inner shaft and changes the length of the outer shaft from the fixed reference point to the distal end of the outer shaft, wherein the inner shaft, outer shaft, and the implantation depth controlling element are configured such that adjustment of the implantation depth controlling element does not uncover a heart valve prosthesis disposed within the outer shaft.

2. The valve introducer of claim 1, wherein the implantation depth controlling element comprises:
   an outer cylinder; and
   an inner cylinder, wherein the outer cylinder and the inner cylinder share a common longitudinal axis,
   wherein the outer cylinder and the inner cylinder are configured to be twisted in opposite directions relative to each other to increase or decrease the length of the implantation depth controlling element.

3. The valve introducer of claim 2, wherein the outer cylinder has interior threads, and
   the inner cylinder has exterior threads which mate with the interior threads of the outer cylinder.

4. The valve introducer of claim 1, wherein the adjustable deployment mechanism further comprises a depth gauge, wherein the depth gauge indicates the length the tubular element extends beyond the fixed reference point.

5. The valve introducer of claim 1, wherein the adjustable deployment mechanism further comprises a spring configured to provide tactile feedback to the deployment element during deployment of the heart valve prosthesis.

6. The valve introducer of claim 1, wherein the adjustable deployment mechanism further comprises a cannula engagement surface.

7. The valve introducer of claim 6, wherein the cannula engagement surface comprises a locking mechanism configured to couple the adjustable deployment mechanism to a cannula such that the tubular element extends through the cannula.

8. The valve introducer system of claim 1, further comprising a cannula, the cannula comprising a fastening element configured to couple the cannula to an outside surface of an aorta, wherein the tubular element extends through the cannula.

9. A method of implanting a heart valve prosthesis with a valve introducer, the valve introducer comprising:
   a tubular element configured to deliver a heart valve prosthesis, wherein the tubular element includes an outer shaft and an inner shaft, the tubular element having a first length extending from a fixed reference point on the valve introducer to a distal end of the outer shaft and a second length extending from the fixed reference point to a distal end of the inner shaft; and
   an adjustable deployment mechanism comprising:
      a deployment element; and
      an implantation depth controlling element having a distal end and an adjustable length; and
   the method comprising:
   adjusting the length of the implantation depth controlling element of the valve introducer to adjust the first length and the second length of the tubular element from the fixed reference point to the distal end of outer shaft and the distal end of the inner shaft, respectively, such that the tubular element of the valve introducer will extend a predetermined depth from a predetermined insertion point through a wall of an aorta to a predetermined implantation site within the aorta;
   loading the heart valve prosthesis into a capsule at the distal end of the tubular member;
   inserting the tubular member of the valve introducer into the aorta to thereby deliver the heart valve prosthesis to the predetermined implantation site;
   activating the deployment element to move the outer shaft relative to the inner shaft to deploy the heart valve prosthesis; and
   removing the tubular member from the aorta.

10. The method of claim 9, wherein the implantation depth controlling element comprises an outer cylinder with interior threads and an inner cylinder with exterior thread, wherein the outer cylinder and the inner cylinder share a common longitudinal axis, and wherein the step of adjusting the length of the implantation depth controlling element comprises twisting the outer cylinder and the inner cylinder in opposite directions relative to each other about the common longitudinal axis.

11. The method of claim 9, further comprising locking the implantation depth controlling element after adjusting the length.

12. The method of claim 9, further comprising fastening a cannula to an outside surface of the aorta and coupling the valve introducer with the cannula such that the tubular member extends through the cannula and into the aorta through the insertion point.

13. The method of claim 9, further comprising using medical imaging to calculate the depth between the insertion point and the implantation site.

14. The method of claim 9, further comprising displaying the depth the tubular element will extend into the aorta on a depth gauge disposed on the implantation depth controlling element.

15. The method of claim 9, further comprising using medical imaging to locate the distal end of the tubular element within the aorta prior to deployment of the heart valve prosthesis.

16. The method of claim 9, further comprising adjusting the implantation depth controlling element after the tubular element is within the aorta.

17. The method of claim 9, further comprising placing a valve at an insertion point on the aorta to prevent blood from escaping the body.

18. The method of claim 9, further comprising placing a patient under extracorporeal circulation.

19. The method of claim 9, wherein the heart valve prosthesis is self-expanding.

20. The method of claim 9, further comprising inflating a balloon to expand the heart valve prosthesis upon deployment.

* * * * *